(12) United States Patent
Grek et al.

(10) Patent No.: US 7,403,284 B2
(45) Date of Patent: Jul. 22, 2008

(54) INTEGRATED OPTICS BASED HIGH-RESOLUTION SPECTROPHOTOMETER

(75) Inventors: Boris Grek, Hayward, CA (US); Saurav Das, Fremont, CA (US)

(73) Assignee: ANDevices, Inc., Fremont, CA (US)

( * ) Notice: Subject to any disclaimer, the term of this patent is extended or adjusted under 35 U.S.C. 154(b) by 102 days.

(21) Appl. No.: 11/015,482

(22) Filed: Dec. 16, 2004

(65) Prior Publication Data

US 2006/0132764 A1   Jun. 22, 2006

(51) Int. Cl.
*G01J 3/28* (2006.01)
*G01J 3/30* (2006.01)
*G02B 6/34* (2006.01)

(52) U.S. Cl. ............. 356/326; 356/328; 356/319; 356/317; 356/246; 385/37; 385/124

(58) Field of Classification Search ........ 356/326, 356/328, 246, 317, 319, 320; 385/12, 14, 385/37, 124
See application file for complete search history.

(56) References Cited

U.S. PATENT DOCUMENTS

| | | | | |
|---|---|---|---|---|
| 5,442,169 | A * | 8/1995 | Kunz | 250/227.21 |
| 5,615,008 | A * | 3/1997 | Stachelek | 356/301 |
| 5,822,472 | A * | 10/1998 | Danielzik et al. | 385/12 |
| 6,303,934 | B1 * | 10/2001 | Daly et al. | 250/339.02 |
| 6,346,376 | B1 * | 2/2002 | Sigrist et al. | 435/5 |
| 6,429,022 | B1 * | 8/2002 | Kunz et al. | 436/164 |
| 6,657,723 | B2 * | 12/2003 | Cohen et al. | 356/328 |
| 6,785,433 | B2 * | 8/2004 | Tiefenthaler | 385/12 |
| 6,818,886 | B2 * | 11/2004 | Tiefenthaler | 250/282 |
| 6,881,979 | B2 * | 4/2005 | Starikov et al. | 257/80 |
| 6,956,651 | B2 * | 10/2005 | Lackritz et al. | 356/445 |

OTHER PUBLICATIONS

Duebendorfer et al, Compact integrated optical immunosensor using replicated chirped gratin coupler sensor chips, Apr. 1998, Applied Optics, v. 37, No. 10, pp. 1890-1894.*

* cited by examiner

*Primary Examiner*—L. G Lauchman
(74) *Attorney, Agent, or Firm*—MacPherson Kwok Chen & Heid LLP (57) ABSTRACT

A spectrophotometer capable of high spectral resolution (e.g., in the GHz range) is presented. The spectrophotometer includes a container for holding a sample, an arrayed-waveguide grating coupled to the sample holder, and a detector array coupled to the arrayed-waveguide grating. The arrayed-waveguide grating may be a monolithic chip, and the container may be integrated into the chip. An integrated container may be a microfluidic channel formed through the layers in the chip and positioned in such a way that light is transferable from the microfluidic channel to the waveguides of the arrayed-waveguide grating.

The invention is also a method of making the spectrophotometer. The method entails providing an arrayed-waveguide grating having an input end and an output end, coupling a container to the input end, wherein the container is capable of holding a sample, and coupling a detector array to the output end of the arrayed-waveguide grating.

43 Claims, 9 Drawing Sheets

INTEGRATED OPTICS BASED HIGH-RESOLUTION SPECTROPHOTOMETER

BACKGROUND

1. Field of Invention

This invention pertains to spectrophotometers in general and particularly to high-resolution spectrophotometers.

2. Related Art

Spectroscopy is a widely used technique for analyzing various substances based on the fact that different substances show different absorption and emission bands.

Figure 1:
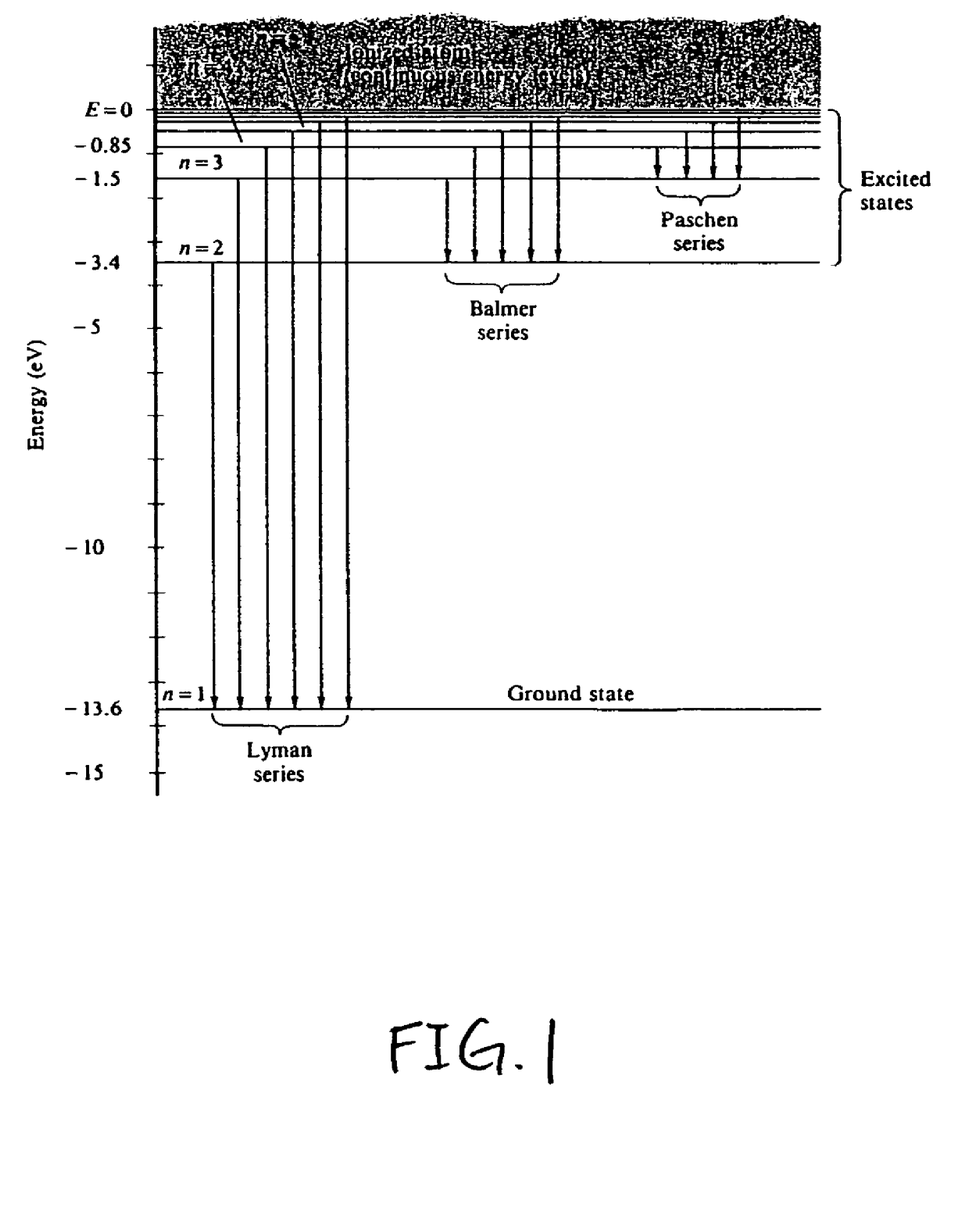
FIG. 1 is an energy-level diagram for the hydrogen atom.

FIG. 1 is an energy-level diagram for the hydrogen atom, showing origin of spectral lines for the Lyman, Balmer, and Paschen series. The quantum number n that labels the orbit radii also labels the energy levels. The lowest energy level, or the lowest "state," is often referred to as the ground state (n=1). The higher states (n>1) are referred to as excited states. When an electron in an excited state jumps down to a lower state, it may give off energy in the form of radiation (e.g., a photon). Since the energy levels are quantized, the states that are involved in the jump can be determined based on the wavelength of the radiation that is emitted. For example, an electron jumping from n=3 to n=2 in the hydrogen atom give rise to a 656-nm line in the Balmer series, while an electron jumping from n=4 to n=2 would give rise to the 486-nm line. The emission is termed fluorescence and the transition between to states is said to be spin allowed if the states have the same spin multiplicity (i.e., both are singlets or both are triplets). If the spin multiplicity changes in the transition, the emission is termed phosphorescence.

Spectroscopy usually entails exciting a sample, for example by passing radiation through it, and determining the wavelengths that are released by the sample. The released emission band includes a pattern of varying intensities at different wavelengths, indicating the wavelengths where emission occurred.

Emission occurs following an absorption event if the upper state is not relaxed by a nonradiative collisional process (called "quenching"). In some cases, absorption, rather than emission, spectra is used in spectroscopy. To use absorption spectroscopy, radiation of known wavelength is passed through a sample. The radiation excites at least some of the electrons in the orbitals of the sample, which absorb energy to rise to a higher energy state. Due to some of the radiation being absorbed, the energy level of the radiation is lower at certain wavelengths after passing through the sample. The intensity pattern across the predetermined wavelength range is referred to as an absorption band, which shows the wavelengths at which absorption occurred.

The absorption band of a substance generally consists of several absorption bands arising from different vibrational motions of the molecule. Within each vibrational energy level are rotational energy levels. Since rotational energy levels are spaced closer together than the vibrational energy levels, a higher resolution is needed to observe the rotational energy levels.

Currently, the emission/absorption bands are determined by using a spectrophotometer that includes a grating and one or more detectors. Sometimes, a prism is used instead of the grating. The grating/prism separates the radiation from the sample into multiple rays based on wavelength, and each of the wavelength-specific rays is directed to a radiation sensor/detector. Various mirrors and other optical components are used to properly direct each radiation beam to the sensor/detector.

One of the disadvantages of the grating-based spectroscopy is that it is inconvenient to use when a high resolution is desired. To split the radiation from the sample into high-resolution wavelengths, multiple layers of grating/prism may be necessary. The increase in the number of gratings undesirably leads to a bulkier equipment and creates greater chances of inaccuracy. A compact spectrophotometer that can achieve a high resolution is desired.

SUMMARY

In one aspect, the invention is a spectrophotometer that includes a container for holding a sample, an arrayed-waveguide grating coupled to the sample holder, and a detector array coupled to the arrayed-waveguide grating.

In another aspect, the invention is a method of making a spectrophotometer. The method entails providing an arrayed-waveguide grating having an input end and an output end, coupling a container to the input end, wherein the container is capable of holding a sample, and coupling a detector array to the output end of the arrayed-waveguide grating.

In yet another aspect, the invention is a method of analyzing a molecule. The method entails passing a beam of radiation through the molecule such that the beam includes a pattern of varying intensities within a predetermined wavelength range after passing through the molecule. The beam is fed to an arrayed-waveguide grating that separates the beam according to wavelength and outputs wavelength-specific sub-beams. By determining the intensity of each of the wavelength-specific sub-beams, information about the molecule may be obtained.

DETAILED DESCRIPTION OF THE PREFERRED EMBODIMENT(S)

Embodiments of the invention are described herein in the context of a silicon chip with AWG formed thereon. However, it is to be understood that the embodiments provided herein are just preferred embodiments, and the scope of the invention is not limited to the applications or the embodiments disclosed herein.

A "fluid," as used herein, includes liquid and gas. As used herein, a "spectrophotometer" is a device that is capable of measuring the wavelength and/or the intensity of radiation. "Silica" is intended to mean any pure or doped form of $SiO_2$ including but not limited to glass, quartz, and pyrex. A sample is "excited" when one or more of its electrons change their energy state by absorbing/emitting radiation.

Figure 2:
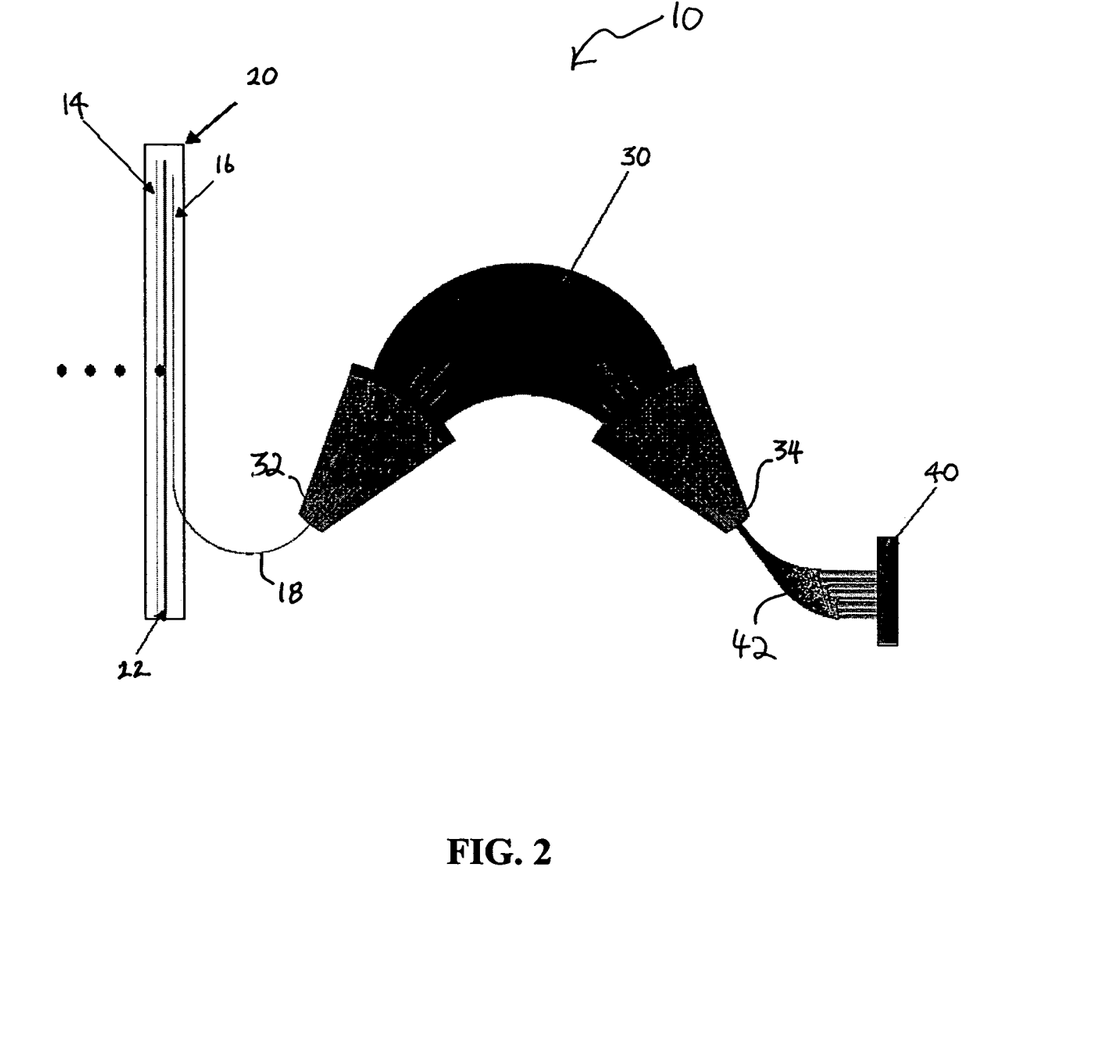
FIG. 2 is a schematic depiction of an AWG-based spectrophotometer in accordance with the invention.

FIG. 2 is a schematic depiction of an AWG-based spectrophotometer 10 in accordance with the invention. The spectrophotometer 10 includes a sampler 20, an arrayed-waveguide grating (AWG) 30, and a detector array 40. The AWG 30 has an input end 32 and an output end 34. The input end 32 is coupled to the sample container 20, and the output end 34 is coupled to the detector array 40.

The sampler 20 includes a container 22 for holding the sample. The sample may be a fluid or a solid. If the sample is a fluid, it may flow through the container 22 or be stagnantly contained therein. The container 22 may be integrated onto the same chip as the AWG 30 or be separate from the chip. If the container 22 is separate from the chip, the container 22 may be any of a variety of commercially available containers that holds the sample, allows the sample to be excited, and allows the emitted light to be guided to the AWG 30. An off-the-chip-type container 22 that is separate from the chip may be of the disposable type.

If the container 22 is integrated with the chip, the container 22 may be a micro-fluidic channel etched into the silica layer of the chip (see FIGS. 5A, 5B, 5C, and 6 below). Flow control actuators may be on the chip or off the chip. The container 22 may be cleaned between runs by running an appropriate fluid (e.g., an alcohol) through the channels 26.

An excitation guide 14 typically carries the light from a radiation source and transfers the radiation onto the sample in the sample container 22. The sample, upon receiving the radiation, becomes excited and its electrons jump up to a higher state. If the electrons fluoresce/phosphoresce, an emission band is generated in the radiation exiting the sample container 22. If the electrons are quenched so that there is substantially no fluorescence/phosphorescence, an absorption band is generated in the radiation exiting the sample container 22. The radiation that passed through the sample is channeled into the AWG 30 via a pickup guide 16 and, if the sample container 22 and the AWG 30 are on separate chips, into an optical fiber 18. The excitation guide 14 may be a normal waveguide just like the core waveguides that make up the AWG 30.

Light traveling in the excitation guide 14 is transferred to the sample container 22 in a number of ways. In a first embodiment, evanescent wave coupling is used for the light transfer. In evanescent wave coupling, a coupling waveguide (not shown) is positioned close to the sample container 22 so that the light "transfers" or "couples over" to the container 22 through a coupling region. In a second embodiment, the light transfer from the excitation guide 14 to the container 22 is assisted by gratings at the junction of the excitation guide 14 and the sample container 22. In a third embodiment, MEMS mirrors are used to reflect the excitation light into the sample container 22. The mirrors are switched away when excitation is not needed.

The pickup guide 16 couples the light emitted by the sample in the container 22 to the AWG 30 in a manner similar to how the light is coupled from the excitation guide 14 to the container 22. Evanescent wave coupling, one or more gratings, or MEMS mirrors may be used as part of the pickup guide 16, as described above. The width of a sample container 22 is typically in the range of 1-100 μm. The widths of the excitation and pickup guides are typically in the range of 1-10 μm.

Excitation could be caused directly from a light source, with the light source situated off the chip and shone onto the container 22 with help of micro optics, fiber, or simple butt coupling. Alternatively, the light source could be on the same chip as the AWG 30. In the latter case, the entire chip needs to be on a different material such as III-V materials like GaAs or InP. Alternatively, the light source and the chip could be integrated in a hybrid way, for example by forming the light source on a III-V material and the AWG chip is on a silica-on-silicon ($SiO_2$-on-Si) material. The light source emits at a frequency that is higher than the excitation energy of the band transitions of the sample. For example, a GaN-based LED emits blue light and can therefore excite band transitions in the infra-red regions.

The AWG 30 includes an array of waveguides that are of varying length. The waveguides vary in length by increments of $\Delta l$ such that, if there were seven waveguides, their lengths would be $x+3\Delta l$, $x+2\Delta l$, $x+\Delta l$, $x$, $x-\Delta l$, $x-2\Delta l$, and $x-3\Delta l$. The waveguides in the AWG 30 having different lengths, signals traveling through different waveguides experience different amounts of time delay in passing through the waveguides. The interference and diffraction caused by the different amounts of delay in each waveguide causes the radiation components having different wavelengths to emerge at different angles from the output end 34.

At the output end 34, radiation components that have the same wavelength are directed into the same one of output waveguides 42. Thus, different output waveguides 42 carry radiation of different wavelengths. The detector array 40 receives the wavelength-specific radiation components from the output waveguides 42. The detector array 40 is coupled to the output waveguides 42 such that radiation traveling through one of the output waveguides 42 is received by one of the detectors in the detector array 40. This way, the wavelength of the radiation that is received by a detector may be determined based on which detector received the particular beam of radiation. If the detectors in the detector array 40 are photodetectors, the intensity of the electrical signal produced by each of the detectors provides information about the intensity of the radiation components. The detector array 40 may be integrated on the same chip as the AWG 30, in silicon or InGaAs.

It is possible to simultaneously connect multiple sample containers 22 to the AWG 30. The AWG 30 may have multiple inputs where the incoming wavelengths on each of the inputs could be made to de-multiplex into different sets of output waveguides/detectors. Alternatively, one input (and correspondingly the same set of output detectors) may be used for multiple channels by connecting the input to the N channels via an N×1 switch.

Figure 3:
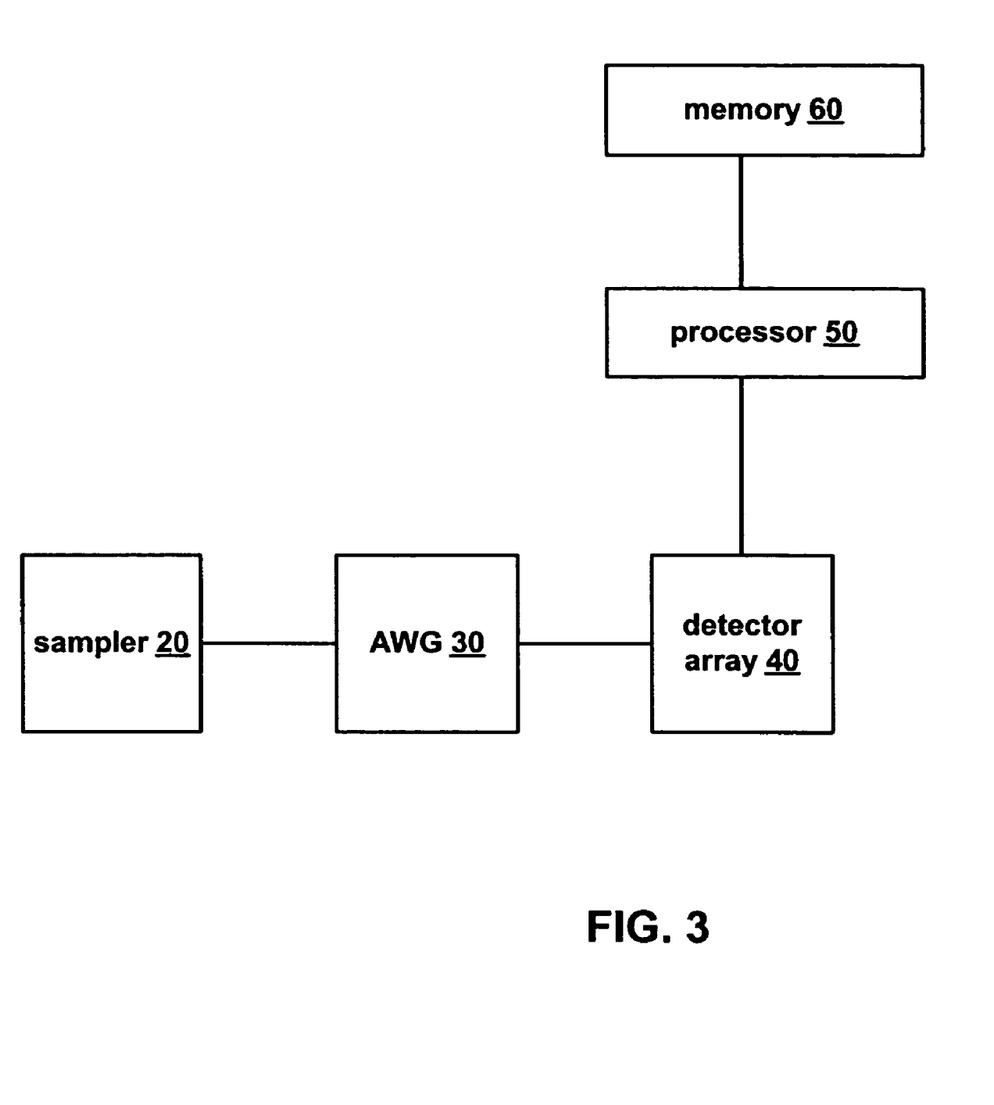
FIG. 3 is a schematic illustration of the spectrophotometer in accordance with the invention.

FIG. 3 is a schematic illustration of the spectrophotometer 10. A processor 50 is coupled to the detector array 40 for processing the information received by the detector array 40 into an emission/absorption spectrum that can be used for identifying the sample. The processor identifies the presence and absence of a radiation component at each wavelength within the predetermined range of wavelengths. Optionally, there may also be a memory 60 that stores emission/absorption band information for a set of molecules. In embodiments that include the memory 60, the processor may use the stored information to identify the sample substance(s), for example by comparing the obtained emission/absorption band against each of the stored information in the memory to find a match.

The sample may contain one or more types of molecules. Various modifications may be made to the spectrophotometer 10 as needed. For example, where the sample is a self-fluorescing material, the excitation guide 14 is not necessary.

Figure 4:
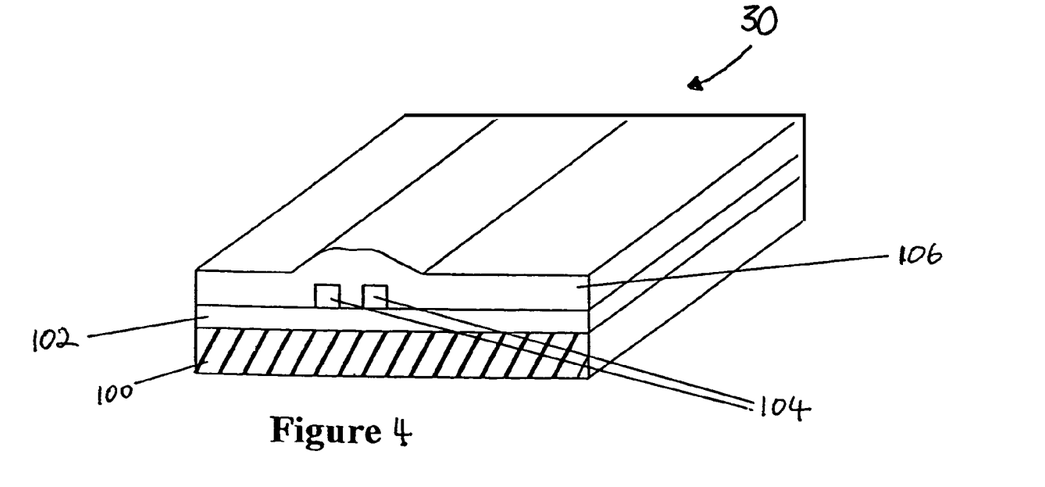
FIG. 4 is a perspective view of the AWG 30 in the form of a monolithic chip, in accordance with an embodiment of the invention.

FIG. 4 is a perspective view of the AWG 30 in the form of a monolithic chip, in accordance with an embodiment of the invention. The silica waveguide is formed by initially depositing a lower cladding layer 102 on a silicon or silica substrate 100, for example by chemical vapor deposition (CVD) or oxidation. The lower cladding layer 102 is about 2-20 μm thick. The lower cladding layer 102 includes pure $SiO_2$ or $SiO_2$ doped to a dopant level of 1-10 wt. %. If the substrate is a quartz glass or fused silica, it may function as the lower cladding layer 102 as well as the substrate.

A layer of doped silica is deposited on top of the lower cladding layer 102 to form a core layer that is about 1-10 μm high. Deposition may be performed with any well-known methods including but not limited to CVD. Examples of dopants for the core layer 104 include $P_2O_5$, $GeO_2$, and $TiO_2$, and the dopant level is typically 1-20 wt. %. The core layer is patterned or sculpted into core regions 104 required by the optical circuits, by using photolithographic techniques similar to those used in integrated circuit fabrication. The refractive index of the core regions 104 is about 0.2-2% higher than that of the lower cladding layer 102 so that light signals stay "contained" in the core regions 104 without significant loss. The core regions 104 are each of a substantially constant width or diameter (e.g., 5 μm×5 μm).

Usually, a top cladding layer 106 is deposited on the patterned core layer. The upper cladding layer 106 is about 2-20 μm thick. The upper cladding layer 106 is either pure silica or silica doped with $P_2O_5$ or $B_2O_3$ to a dopant level of about 0-15 wt.%. Since the core regions 104 are patterned, the upper cladding layer 106 separates the core regions 104 from each other. The refractive index of the upper cladding layer 106 may be about the same as that of the lower cladding layer 102. More details about the monolithic AWG 30 are provided in U.S. Published application Ser. No. 10/427,558 filed on Apr. 30, 2003, which is incorporated by reference herein.

The size of the AWG 30 chip is typically in the range of 40 mm×30 mm×1 mm. In spite of the compact size, the AWG 30 can achieve spectral resolution in the GHz range (i.e., in the order of a tenth of a nm). For example, the AWG 30 could be designed for a frequency spacing as narrow as 25 GHz, 50 GHz, or 100 GHz.

Figure 5A:
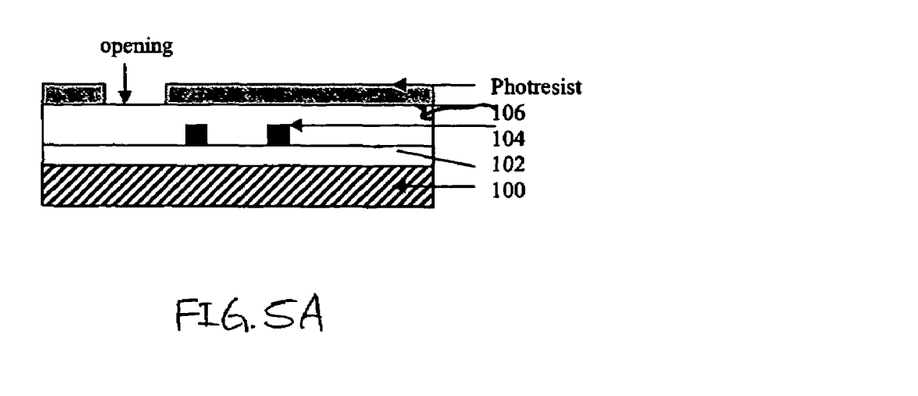
FIG. 5A, FIG. 5B, and FIG. 5C is a schematic depiction illustrating the formation of a channel in the monolithic chip of FIG. 4.
Figure 5B:
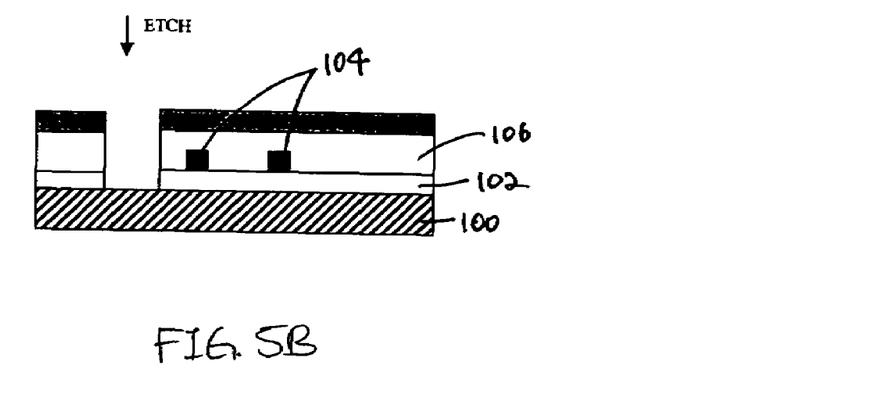
Figure 5C:
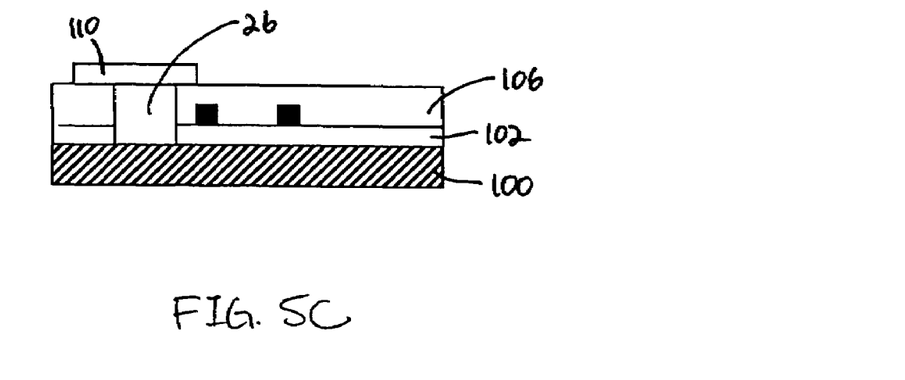

FIGS. 5A, 5B, and 5C depict the formation of a microfluidic channel 26 in the monolithic chip of FIG. 4 to form a container 22 that is integrated with the AWG chip. As shown, the microfluidic channel 26 is etched after the top cladding 106 is deposited. Using conventional lithographic techniques, the microfluidic channel pattern may be traced on the photoresist layer covering the top cladding 106. As shown in FIG. 5A, the microfluidic channel trace is "open" in the photoresist layer. As shown in FIG. 5B, this "opening" is used to etch the layers under it and form the microfluidic channel 26. Depending on the need, just the upper cladding 106 or both the upper cladding 106 and the lower cladding 102 may be etched. The walls of the channel 26 may be coated with a protective or nonreactive material if desired, and the photoresist is removed. The channel 26 may be covered or capped by a pyrex lid 110, as shown in FIG. 5C. A microfluidic channel 26 typically ranges between about 1 to about 100 μm in width.

Figure 6:
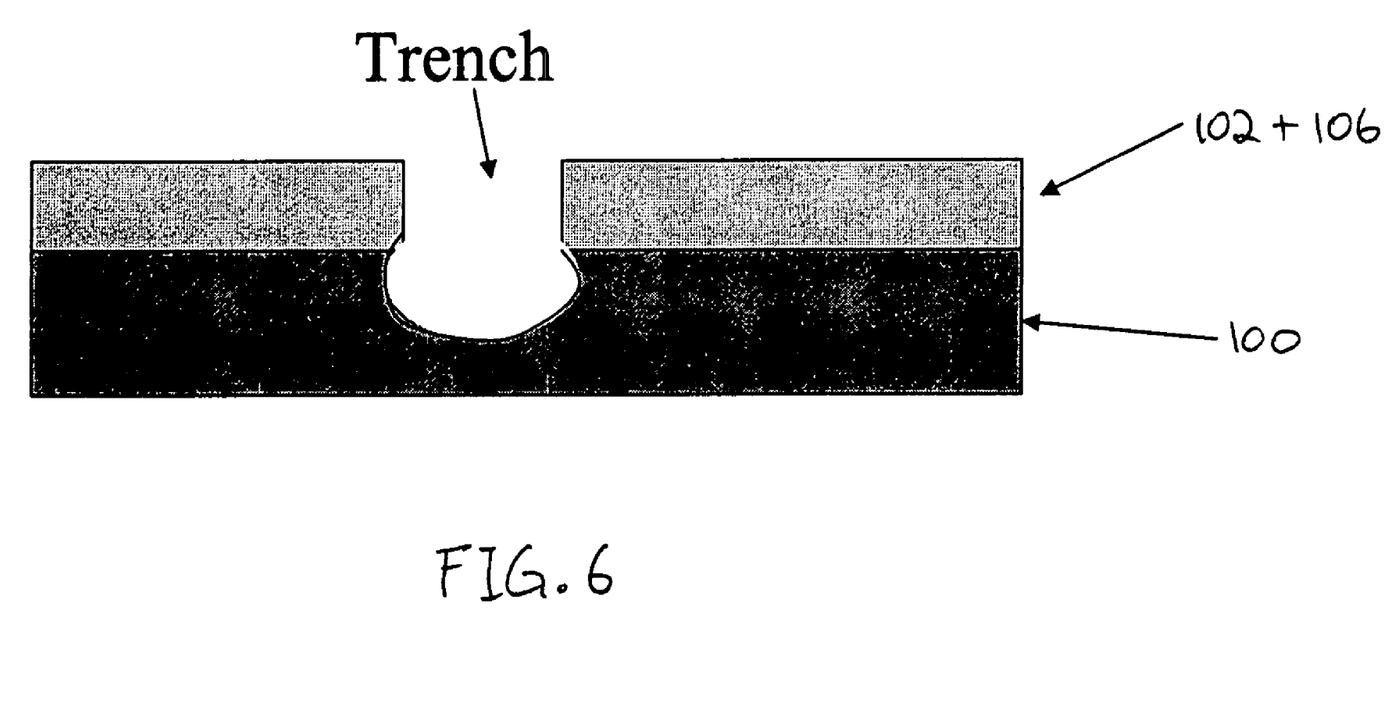
FIG. 6 is an alternative type of channel that may be formed in the monolithic chip of FIG. 4.
Figure 7:
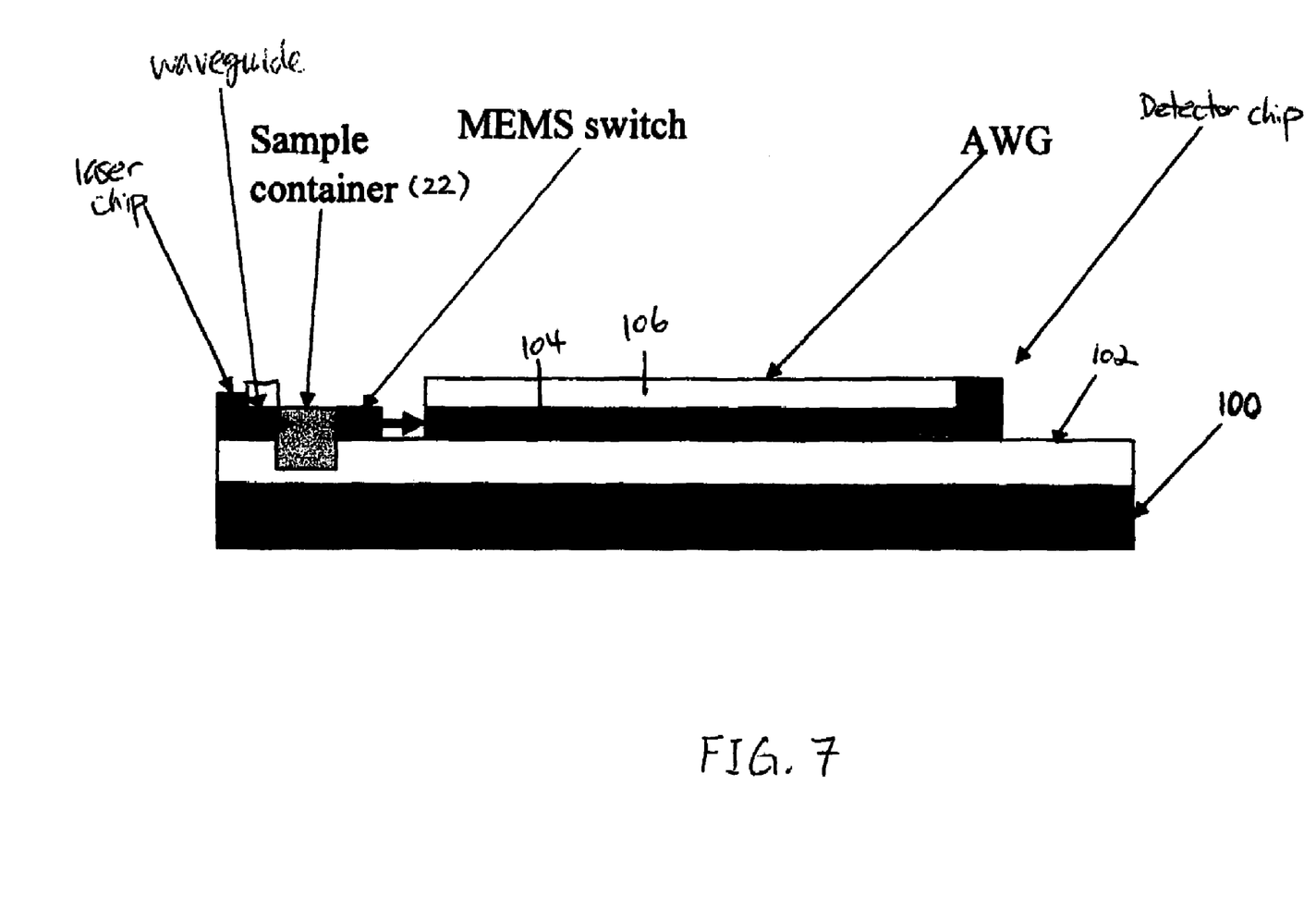
FIGS. 7, 8, and 9 are side views of three embodiments of the spectrophotometer of the invention.
Figure 8:
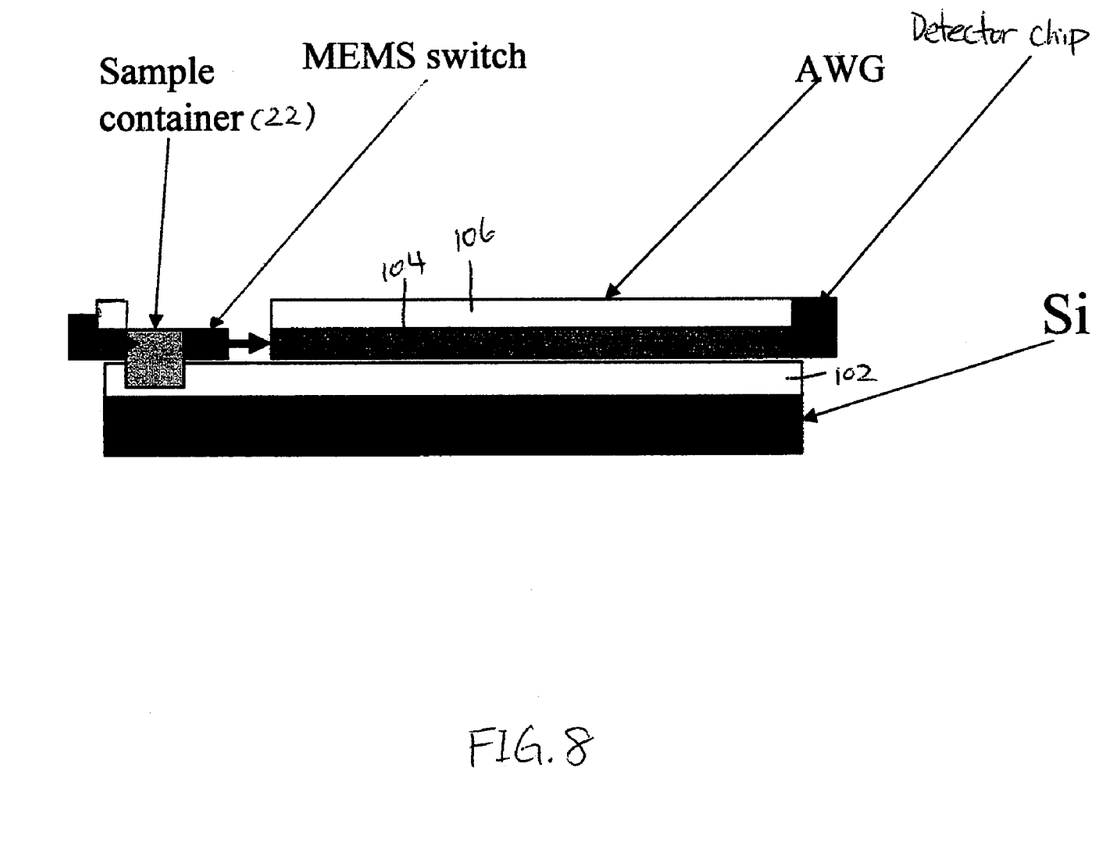
Figure 9:
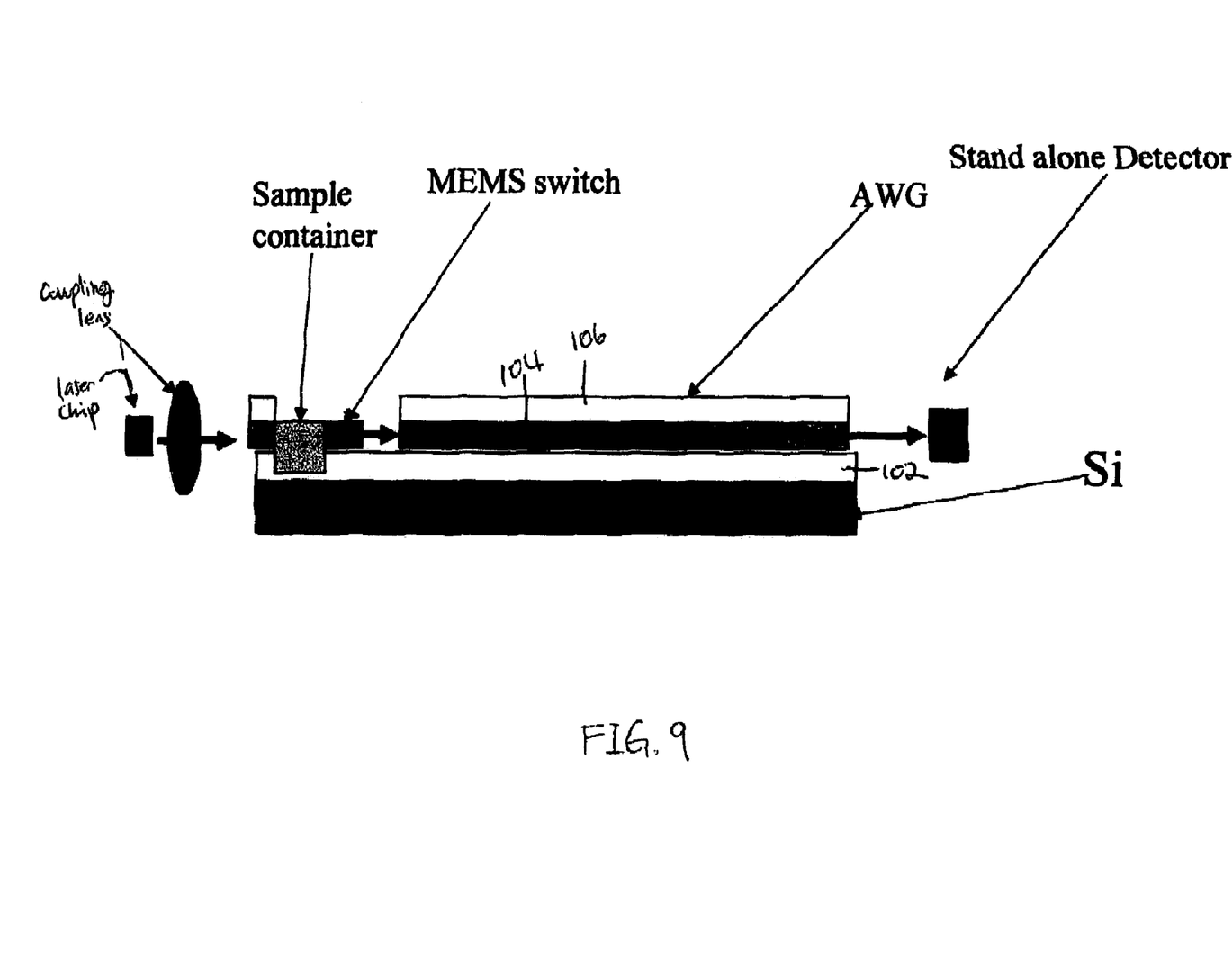

FIG. 6 is a schematic depiction of an alternative type of microfluidic channel 26. Unlike the microfludic channel in FIGS. 5A-5C, which only extends through the lower and upper cladding layers 102, 106, the channel of FIG. 6 extends partway through the substrate 100. As mentioned above, the substrate 100 may be made of silicon or silica. A person of ordinary skill in the art will understand when to use the channel of FIG. 6 and when to use the channel of FIGS. 5A-5C depending on the application. The monolithic chip may include layers that are made of materials other than silicon and silica. In that case, the channel 26 may be etched through those other layers as needed.

Although preferred embodiments of the present invention have been described in detail hereinabove, it should be clearly understood that many variations and/or modifications of the basic inventive concepts herein taught which may appear to those skilled in the present art will still fall within the spirit and scope of the present invention.

What is claimed is:

1. A spectrophotometer comprising:
   a container for holding a sample, wherein the container allows radiation to pass through the sample such that the sample emits an absorption/emission band by fluorescence/phosphorescence;
   an arrayed-waveguide grating coupled to the sample holder to receive the absorption/emission band from the container; and
   a detector array coupled to the arrayed-waveguide grating.

2. The spectrophotometer of claim 1, wherein the arrayed-waveguide grating is a monolithic silica chip.

3. The spectrophotometer of claim 2, wherein the silicon chip comprises:
   a substrate containing either silicon or silica;
   a lower cladding layer;
   an upper cladding layer; and
   a core region formed between the lower cladding layer and the upper cladding layer, the core region having a refractive index that is higher than that of the lower cladding layer.

4. A spectrophotometer comprising:
   a container for holding a sample;
   an arrayed-waveguide grating coupled to the sample holder, wherein the arrayed-waveguide grating is a monolithic silica chip having:
      a lower cladding layer;
      an upper cladding layer; and
      a core region formed between the lower cladding layer and the upper cladding layer, the core region having a refractive index that is higher than that of the lower cladding layer; and
   a detector array coupled to the arrayed-waveguide grating, wherein the container comprises a cavity in one or both of the lower cladding layer and the upper cladding layer.

5. The spectrophotometer of claim 4, wherein the cavity is in the lower cladding layer, the upper cladding layer, and the substrate.

6. The spectrophotometer of claim 4, wherein the container further comprises a silica lid placed over the cavity to create a microfluidic channel.

7. The spectrophotometer of claim 1 further comprising an excitation guide that transfers radiation to the sample.

8. The spectrophotometer of claim 7 further comprising a coupling waveguide positioned sufficiently close to the excitation guide and the container so as to transfer the radiation from the excitation guide to the sample.

9. The spectrophotometer of claim 7 further comprising a MEMS mirror positioned to guide the radiation from the excitation guide toward the container.

10. The spectrophotometer of claim 1 further comprising a light source that emits radiation at the sample.

11. The spectrophotometer of claim 10, wherein the light source and the arrayed-waveguide grating are on a single chip.

12. The spectrophotometer of claim 11, wherein the chip is made of a III-V semiconductor material.

13. The spectrophotometer of claim 10, wherein the light source is formed on a III-V semiconductor material and the arrayed-waveguide grating is formed on a silica-on-silicon chip.

14. The spectrophotometer of claim 1, wherein the arrayed-waveguide grating is coupled to the container with an optical fiber.

15. The spectrophotometer of claim 14, wherein radiation coming from the container is picked up by the optical fiber and transmitted to the arrayed-waveguide grating.

16. The spectrophotometer of claim 14, wherein the arrayed-waveguide grating receives radiation through the optical fiber and separates the radiation according to wavelength.

17. The spectrophotometer of claim 1 further comprising a set of output waveguides coupling the arrayed-waveguide grating to the detector array, wherein each one of the output waveguides is coupled to one detector in the detector array.

18. The spectrophotometer of claim 1 further comprising a processor coupled to the detector array, wherein the processor identifies the sample based on a pattern of intensity variation as a function of wavelength as received from the detector array.

19. The spectrophotometer of claim 1, wherein the detector array comprises a plurality of photodetectors.

20. The spectrophotometer of claim 1, wherein the container is a first container, further comprising a second container coupled to the arrayed-waveguide grating.

21. The spectrophotometer of claim 20, wherein the input end is a first input end, further comprising a second input end of the arrayed-waveguide grating, wherein the first input end receives signals from the first container and the second input end receives signals from the second container.

22. The spectrophotometer of claim 20 further comprising a switching mechanism positioned near the junction of the first and the second containers and the arrayed-waveguide grating to selectively transfer signals from one of the containers to the arrayed-waveguide grating.

23. A method of making a spectrophotometer, the method comprising:
    providing an arrayed-waveguide grating having an input end and an output end;
    coupling a container to the input end, wherein the container is capable of holding a sample and allowing radiation to pass through the sample such that the sample emits an absorption/emission band by fluorescence/phosphorescence; and
    coupling a detector array to the output end of the arrayed-waveguide grating.

24. The method of claim 23 further comprising making the arrayed-waveguide grating in the form of a monolithic chip.

25. The method of claim 24, wherein making the arrayed-waveguide grating comprises:
    providing a substrate containing either silicon or silica;
    forming a lower cladding layer on the substrate;
    forming a core region on the lower cladding layer, wherein the core region has a refractive index that is higher than that of the lower cladding layer; and
    depositing an upper cladding layer over the core region.

26. A method of making a spectrophotometer, the method comprising:
    providing an arrayed-waveguide grating having an input end and an output end, wherein the arrayed-waveguide grating is in the form of a monolithic chip that is made by:
        providing a substrate containing either silicon or silica;
        forming a lower cladding layer on the substrate;
        forming a core region on the lower cladding layer, wherein the core region has a refractive index that is higher than that of the lower cladding layer; and
        depositing an upper cladding layer over the core region; and
    coupling a container to the input end, wherein the container is capable of holding a sample; and
    coupling a detector array to the output end of the arrayed-waveguide grating, wherein coupling the container to the input end of the arrayed-waveguide grating comprises forming a cavity in one or both of the lower cladding layer and the upper cladding layer.

27. The method of claim 26, wherein coupling the container to the input end of the arrayed-waveguide grating further comprises forming a cavity in the substrate.

28. The method of claim 27, wherein coupling the container to the input end of the arrayed-waveguide grating comprises placing a silica lid over the cavity to form a microfluidic channel.

29. The method of claim 23 further comprising coupling an excitation guide to the container, wherein the excitation guide emits radiation capable of exciting the sample.

30. The method of claim 29, wherein coupling the excitation guide to the container comprises placing a coupling waveguide sufficiently close to the excitation guide and the container so that the coupling waveguide transfers radiation from the excitation guide to the container.

31. The method of claim 29, wherein coupling the excitation guide to the container comprises placing a grating near the excitation guide and the container to transfer the radiation from the excitation guide to the container.

32. The method of claim 29, wherein coupling the excitation guide to the container comprises using a MEMS mirror to reflect the radiation from the excitation guide toward the container.

33. The method of claim 23, wherein coupling the container to the input end comprises using an optical fiber to channel radiation from the container to the input end of the arrayed-waveguide grating.

34. The method of claim 23, wherein coupling the detector array to the output end of the arrayed-waveguide grating comprises coupling one of a plurality of output waveguides to one detector in the detector array.

35. The method of claim 23 further comprising coupling a processor to the detector array, wherein the processor identifies the sample based on a pattern of intensity variation as a function of wavelength as received from the detector array.

36. The method of claim 23, wherein the container is a first container, the sample is a first sample, and the input end is a first input end, further comprising:
    forming a second input end to the arrayed-waveguide grating;
    coupling a second container to the first input end of the arrayed-waveguide grating, wherein the second container is capable of holding a second sample.

37. The method of claim 23, wherein the container is a first container, further comprising placing a switching mechanism near the junction of the first and the second containers and the arrayed-waveguide grating to selectively transfer signals from one of the containers to the arrayed-waveguide grating.

38. A method of analyzing a molecule, the method comprising:
    exciting the molecule to fluorescence/phosphorescence by passing a beam of radiation through the molecule such that the beam includes a pattern of varying intensities within a predetermined wavelength range after passing through the molecule;

feeding the beam to an arrayed-waveguide grating that separates the beam according to wavelength and outputs wavelength-specific sub-beams; and determining an intensity of each of the wavelength-specific sub-beams.

39. The method of claim 38, wherein the arrayed-waveguide grating is a monolithic chip.

40. The spectrophotometer of claim 1, wherein the container, the arrayed-waveguide grating, and the detector are integrated on a single chip.

41. The spectrophotometer of claim 40, wherein the single chip is made of a III-V semiconductor material.

42. The method of claim 23 further comprising integrating the arrayed-waveguide grating, the container, and the detector array on a single chip.

43. The method of claim 42, wherein the single chip is made of a III-V semiconductor material.

* * * * *